United States Patent [19]
Ljevakovic et al.

[11] Patent Number: 5,290,576
[45] Date of Patent: Mar. 1, 1994

[54] TERT-BUTYLOXYCARBONYL-L-TYROSYL-PEPTIDOGLYCAN MONOMER AND $^{125}$I-LABELED DERIVATIVE THEREOF, THEIR PREPARATION AND USE

[75] Inventors: Djurdjica Ljevakovic; Branka Vranesic; Jelka Tomasic; Ivo Hrsak; Branko Ladesic, all of Zagreb, Croatia

[73] Assignees: Pliva Farmaceutska; Kemijska Prehrambena, Croatia

[21] Appl. No.: 810,010

[22] Filed: Dec. 20, 1991

[30] Foreign Application Priority Data

Dec. 21, 1990 [YU] Yugoslavia .................. 2424/90

[51] Int. Cl.$^5$ .................. A61K 37/10; C07H 15/00; C07H 17/00
[52] U.S. Cl. .................. 526/238.2; 526/238.23; 514/8; 536/4.1; 530/322
[58] Field of Search .................. 514/8; 530/322; 526/238.2, 238.23; 536/4.1

[56] References Cited

U.S. PATENT DOCUMENTS 4,310,514 1/1982 Durette .................. 530/322

Primary Examiner—Nathan M. Nutter
Attorney, Agent, or Firm—Pollock, Vande Sande & Priddy

[57] ABSTRACT

The present invention relates to the novel tert-butyloxycarbonyl-L-tyrosylpeptidoglycan monomer

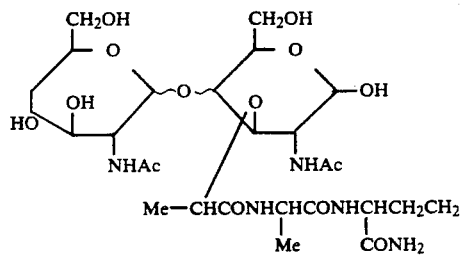

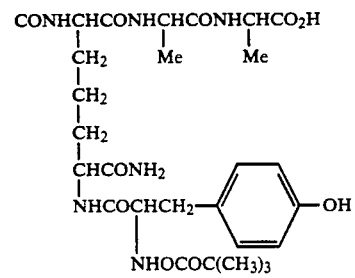

and to its $^{125}$I-labelled Boc-Tyr-PGM derivative; to the preparation and use thereof as pharmaceuticals of immunostimulating and antitumor activity.

8 Claims, No Drawings

TERT-BUTYLOXYCARBONYL-L-TYROSYL-PEPTIDOGLYCAN MONOMER AND 125I-LABELED DERIVATIVE THEREOF, THEIR PREPARATION AND USE

The invention relates to the tert-butyloxycarbonyl-L-tyrosyl-peptidoglycan monomer and $^{125}$I-labelled derivative thereof, to a process for the preparation thereof and to the use of the new compounds of the invention in pharmaceuticals; the tert-butyloxycarbonyl-L-tyrosyl-peptidoglycan monomer is particularly indicated for pharmaceuticals possessing immunomodulating and antitumor activity, whereas the novel $^{125}$I-labelled derivative exhibits anti-PGM antibody binding properties.

It has been known that the peptidoglycan monomer (PGM, GlcNAc-$\beta$-(1→4)MurNAc-L-Ala-D-iGln-[(L)-meso-A$_2$pm-(D)-amide-(L)-D-Ala-D-Ala], which is the smallest repeating unit of the *Brevibacterium divaricum* cell wall peptidoglycan, possesses immunostimulating, antitumor and antimetastatic activities (Tomasic, J. and Hrsak, I. (1988), Peptidoglycan monomer originating from *Brevibacterium divaricatum*—its metabolism and biological activities in the host, in: Surface Structure of Microorganisms and Their Interaction with the Mammalian Host (Schrinner, E., Richmond, M. H., Seibert, G. and Schwartz, U., Eds.), p. 113–121, VCH Verlagsgesellschaft, Weinheim).

It has been known that the formation of the peptide bond may be achieved provided that the amino acid
  a) is first converted into an N-protected amino acid by the introduction of so-called protecting groups,
  b) is activated at the carboxy group,
  c) there is performed a reaction with C-terminally protected amino acid, di-, tri-, or polypeptides, and
  d) the protecting groups of the obtained di-, tri-, or polypeptides are carefully eliminated by means of specific reactions
(Houben-Weyl, Methoden der organischen Chemie, 4. Auflage, herausgegeben von Egon Müller, Synthese von Peptiden I und II, Bd 15/1 und 15/2, Georg Thieme Verlag, Stuttgart 1974).

Further, in polyfunctional molecules of highly complex structure, such as e.g. the peptidoglycan monomer, consisting of disaccharide pentapeptides (the sugar and the peptide moieties)
  a) the hydroxy groups on GLcNAc and MuRNAc (sugar moiety of the molecule), have to be protected and
  b) upon the performed reaction of formation of the peptide bond there has to be performed the deprotection of the sugar moiety.

It has been known as well that the conventional method of inserting the tyrosine into the peptide or protein is the "active ester method", wherein Boc-L-Tyr-ONSu is the acylating component (Assoian, R. K. (1980) Anal. Biochem. 103, 70).

The ever increasing need for new substances of a potentially immunostimulating effect and possible antitumor activity resulted in the conception of the present invention, relating to the novel substance tert-butyloxycarbonyl-L-tyrosyl-peptidoglycan monomer (Boc-Tyr-PGM) of the formula I

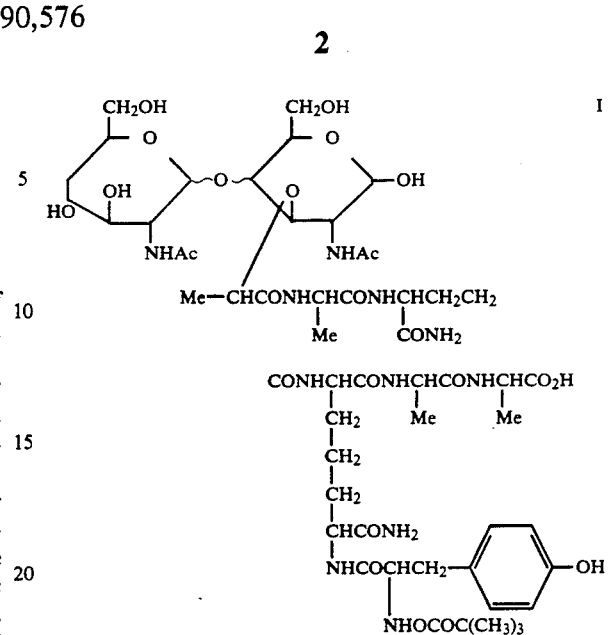

and its [125]-labelled derivative.

The novel derivation of peptidoglycan monomer (I), a compound of increased lipophilicity, makes possible an easier penetration of the substance through the cell walls and a prolonged residual time thereof in the organism. This was achieved by the introduction of the native aromatic amino acid tyrosine into the PGM molecule, whereby from the disaccharide pentapeptide, the disaccharide hexapeptide (Boc-Tyr-PGM), was obtained which was subsequently labelled with radioactive $^{125}$I, thus yielding its derivative

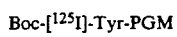

Boc-[$^{125}$I]-Tyr-PGM

In the conception of the process for the preparation of the novel derivative of peptidoglycan monomer there were applied per se known methods of peptide chemistry; yet for the first time the synthesis operated with a completely unprotected molecule of a very complex structure.

The process for the preparation of the novel PGM derivative of the present invention is illustrated by the following reaction scheme:

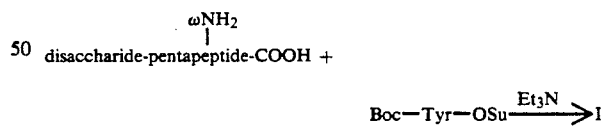

In accordance with the present invention there was performed the regio-selective reaction of Boc-Tyr-Osu with the omega-amino group of the meso-diaminopimelic acid in the PGM molecule, in the presence of triethylamine, yielding the novel derivative disaccharide-hexapeptide, which was first isolated by gel chromatography on a SEPHADEX ® G-25 column and by column chromatography on a silica gel column, whereupon it was completely purified and adapted for biological investigations by means of gel chromatography on BIOGEL ® P-2.

The labelling of Boc-Tyr-PGM with radioactive iodine was performed by means of the standard chloramine T method (Bolton, A.E. (1985), in: Radioiodination Techniques, Second Edition, p. 109, Amersham Int. plc, England).

Upon electrophilic substitution of the phenol ring in ortho-position with respect to the hydroxy group in tyrosine the $^{125}$I-labelled molecule of a high specific activity and sufficient radiochemical stability was obtained.

The process of preparation is represented by the following scheme:

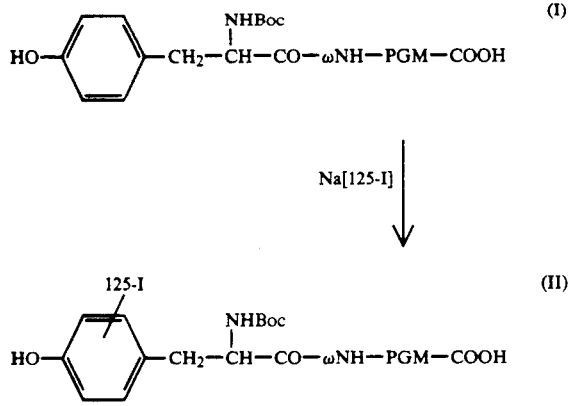

In accordance with the present invention the synthesis of the radioactive iodine-labelled Boc-Tyr-PGM was performed using the standard chloramine T method with Na[$^{125}$I] yielding the iodinated product II, which was isolated by gel chromatography on a SEPHADEX® G-25 column and used in the survey of the antigen-antibody binding reaction.

The novel PGM-derivative disaccharide hexapeptide may be utilized in pharmaceuticals, possessing immunomodulating and antitumor activity, whereas the novel $^{125}$I-labelled derivative may be used as essential component in competitive radioimmunoassay for PGM determination, exhibiting the property of binding anti-PGM antibodies.

The present invention is illustrated by the following Examples:

EXAMPLE I tert-Butyloxycarbonyl-L-tyrosyl-peptidoglycan monomer (I)

The peptidoglycan monomer (PGM, 100 mg, 0.1 mmole) was dissolved in dry dimethylformamide (DMF, 2.6 mL) under the addition of triethylamine (30 μL). Into the cooled (ice-water) solution solid Boc-Tyr-OSu (56 mg, 0.12 m mole) was added in small portions, under stirring. The reaction was left for 16 hours at room temperature, whereupon DMF was evaporated in vacuo, generated by a mechanical pump. The thick syrupous evaporation residue was dissolved in water, acidified with solid citric acid up to pH 3, whereupon it was extracted with ethyl acetate (3 × 10 mL). The aqueous portion was concentrated to 2 mL and loaded on a SEPHADEX® G-25 column (90×2.5 cm) in water. The fractions (3 mL) were investigated for absorbance at 230 nm, and those corresponding to a higher molecular mass compound were combined and evaporated. The obtained glassy residue (110 mg) was dissolved in a 5:3:2:2 mixture of n-butanol, ethanol, NH$_3$ (25%), and water, whereupon it was chromatographed on a silica gel column with the same eluent. The neutralization with HOAc and evaporation of the fractions yielded the product, which was finally purified by means of gel chromatography on a BIOGEL® P-2 column (70×2.5 cm), in with water. The most mobile fractions were combined, concentrated, and lyophilized. There were obtained 58 mg (46%) of the pure Boc-Tyr-PGM (I).

The analysis of amino acids: GlcNH$_2$0.82; MurNH$_2$0.57; Ala, 3; Glu, 1; A$_2$pm, 0.98; Tyr, 0.80.

$^1$H-NMR spectrum (D$_2$O): 1.29 (s, Me$_3$C), 1.34–1.70 (m, partial overlapping with Me$_3$C, 21H, 3×Me-Ala+-lactoyl-Me), 1.89 and 1.98 (2s, 6H, 2×NAc), 6.77 and 7.07 (2d, 2H each, $I_{H,H}$ 8.55 Hz, —C$_6$H$_4$—).

Thin layer chromatography: n-butanol-ethanol-NH$_3$(25%)-water (5:3:2:2), detection with iodine vapours and peptide Reagent, $R_f$=0.5.

EXAMPLE II tert-Butyloxycarbonyl-[$^{125}$I]-L-tyrosyl-peptidoglycan monomer (II)

Into a solution of Boc-Tyr-PGM (5 μg) in phosphate buffer (25 μL, 0.5M, pH 7.5), Na[$^{125}$I] (10 μL, 3.7×10 Bq, 1 mCi) and chloramine T (50 μg) in phosphate buffer (25 μL, 0.25M, pH 7.5) were added, and after 45 seconds the reaction was stopped by the addition of sodium metabisulfite (50 μg) in 25 μL of water. The reaction mixture was immediately loaded on a SEPHADEX® G-25 column (30×1.5 cm), which was previously washed with a solution of human albumin and equilibrated with 0.025M phosphate buffer of pH 7.5, which was utilized in elution. The fractions (2 mL) were tested on radioactivity and those corresponding to Boc-[$^{125}$I]-L-Tyr-PGM were combined. The specific activity of the obtained derivative II: approximately 3.12 MBq/μg (0.087 mCi/μg).

EXAMPLE III

Immunostimulating activity of the tert-butyloxycarbonyl-L-tyrosyl-peptidoglycan monomer (Boc-Tyr-PGM)

The immunostimulating activity of Boc-Tyr-PGM was tested in mice immunized with sheep erythrocytes (sheep red blood cells, SRBC).

Mice (CBA or AKR), five per group, were immunized i.p. with sheep erythrocytes (1×10$^8$ SRBC) in Hanks' solution. One day later (on day +1), the control group of mice receiving i.v. Hanks' solution, whereas the test group of mice was given i.v. 200 μg of Boc-Tyr-PGM in Hanks' solution. As positive control, a group of mice was used, to which 200 μg of peptidoglycan monomer (PGM) in Hanks' solution was administered i.v. Four days later (on day +4), the number of antibody-forming cells (plaque-forming cells, PFC) was determined in the spleen by Jerne's technique (Jerne, N. K., Nordin, A. A., and Henry, C. (1963), The agar plaque tecnique for recognizing antibody producing cells, in: "Cell Bound Antibodies", p. 109, Wistar Institute Press, Philadelphia).

The results are listed in Table I.

TABLE I

| Mice strain | Treatment | PFC Range of individual values | $\bar{X}$ | % |
|---|---|---|---|---|
| CBA | Hanks' | 95,200–238,000 | 188,906 | 100 |
|  | Boc—Tyr—PGM | 257,600–304,266 | 295,866 | 157 |
|  | PGM | 198,800–449,866 | 313,413 | 166 |
| AKR | Hanks' | 20,000–55,200 | 37,388 | 100 |
|  | Boc—Tyr—PGM | 31,730–68,670 | 55,974 | 150 |

TABLE I-continued

| Mice strain | Treatment | PFC Range of individual values | $\bar{X}$ | % |
|---|---|---|---|---|
| | PGM | 27,200–61,070 | 48,668 | 130 |

Boc-Tyr-PGM demonstrated an immunostimulating (adjuvant) activity in both mice strains, in which an approximately 50% increased number of PFC was was detected in comparison with the control group. The effectiveness of Boc-Tyr-PGM was in both tests comparable with the effect of the positive control, i.e. the peptidoglycan monomer.

EXAMPLE IV

Antitumor (antimetastatic) activity of the tert-butyloxycarbonyl-L-tyrosyl-peptidoglycan monomer (Boc-Tyr-PGM)

The antitumor activity of Boc-Tyr-PGM was investigated in mice, inoculated with melanoma B-16.

Mice (C5 7 BL/6, male, 4 months old), five per group, were given i.v. each $1 \times 10^5$ cells of B-16 melanoma on day 0.

One group of mice was chosen as control and was not treated further in any manner. The mice in experimental groups were given i.v. each 1 mg of Boc-Tyr-PGM, according to the following protocol:

1st group—day 3
2nd group—day 7
3rd group—days 3 and 7 (total 2 mg of Boc-Tyr-PGM)

Three mice groups, which received PGM (PLIVA) i.v. according to the same protocol, were chosen as the positive control.

Macroscopically detectable lung metastases were counted on day 23. The results are represented in Table II.

TABLE II

| Treatment | Day | Number $\bar{X}$ | Metastases % | Inhibition % |
|---|---|---|---|---|
| Hanks' | — | 12.4 ± 6.1 | 100 | |
| Boc—Tyr—PGM | 3 | 7.6 ± 1.9 | 61.3 | 38.7 |
| | 7 | 7.2 ± 4.0 | 58.1 | 41.9 |
| | 3 + 7 | 7.0 ± 2.7 | 56.4 | 43.6 |
| PGM (PLIVA) | 3 | 6.2 ± 4.4 | 50.0 | 50.0 |
| | 7 | 5.4 ± 1.7 | 43.5 | 66.5 |
| | 3 + 7 | 5.3 ± 1.7 | 42.7 | 67.3 |

The treatment with Boc-Tyr-PGM caused an antimetastatic effect, resulting in a diminished number of metastases in all treated mice groups (inhibition rate of 37.8%–43.6%). No significant difference in the inhibition rate was observed in mice treated in different periods (on day 3 or 7), as well as with a different total given dose (1 mg on day 3, or total 2 mg on days 3 and 7).

The effect of Boc-Tyr-PGM is comparable to the effect of PGM (PLIVA) used as positive control.

We claim:

1. tert-Butyloxycarbonyl-L-tyrosyl-peptidoglycan monomer of the formula and its $^{125}$I-labelled derivative (Boc-[$^{125}$I]-Tyr-PGM).

2. A process for preparing the tert-butyloxycarbonyl-L-tyrosyl-peptidoglycan monomer of formula (I) of claim 1, characterized in that the tert-butyloxycarbonyl-L-tyrosine-N-hydroxysuccinimidester is condensed with the unprotected peptidoglycan monomer in the presence of triethylamine, whereupon the obtained tert-butyloxycarbonyl-L-tyrosyl-peptidoglycan monomer (Boc-Tyr-PGM) is isolated by gel chromatography, then by column chromatography on a silica gel column.

3. A process as claimed in claim 2, characterized in that Boc-Tyr-PGM is $^{125}$I-labelled by the addition of Na[$^{125}$I] and chloroamine T, and upon stopping the reaction by means of sodium bisulfite, the product is isolated by gel chromatography.

4. A pharmaceutical composition comprising a pharmaceutically effective amount of the tert-butyloxycarbonyl-L-tyrosyl-peptidoglycan monomer of claim 1.

5. The composition of claim 4 wherein said monomer is present in an effective immunostimulating amount.

6. The composition of claim 5 wherein said amount is 200 μg.

7. The composition of claim 4 wherein said monomer is present in an effective antitumor amount.

8. The composition of claim 7 wherein said amount is 1–2 mg.

* * * * *